(12) United States Patent
Derkx et al.

(10) Patent No.: US 11,272,716 B2
(45) Date of Patent: Mar. 15, 2022

(54) BACTERIA

(71) Applicant: CHR. HANSEN A/S, Hoersholm (DK)

(72) Inventors: Patrick Derkx, Tikoeb (DK); Thomas Janzen, Broenshoej (DK); Kim Ib Soerensen, Farum (DK)

(73) Assignee: CHR. HANSEN A/S, Hoersholm (DK)

( * ) Notice: Subject to any disclaimer, the term of this patent is extended or adjusted under 35 U.S.C. 154(b) by 120 days.

(21) Appl. No.: 16/329,727

(22) PCT Filed: Aug. 24, 2017

(86) PCT No.: PCT/EP2017/071352
§ 371 (c)(1),
(2) Date: Feb. 28, 2019

(87) PCT Pub. No.: WO2018/041717
PCT Pub. Date: Mar. 8, 2018

(65) Prior Publication Data
US 2019/0320673 A1      Oct. 24, 2019

(30) Foreign Application Priority Data

Sep. 1, 2016   (WO) ............... PCT/DK2016/000031

(51) Int. Cl.
| | |
|---|---|
| *A23C 19/032* | (2006.01) |
| *A23C 9/123* | (2006.01) |
| *C07K 14/315* | (2006.01) |
| *C12N 1/20* | (2006.01) |
| *C12R 1/46* | (2006.01) |

(52) U.S. Cl.
CPC ........ *A23C 19/0323* (2013.01); *A23C 9/1238* (2013.01); *C07K 14/315* (2013.01); *C12N 1/20* (2013.01); *C12N 1/205* (2021.05); *A23Y 2240/75* (2013.01); *C12R 2001/46* (2021.05)

(58) Field of Classification Search
CPC   A23C 19/0323; A23C 9/1238; C07K 14/315; C12N 1/20; C12R 1/46; A23Y 2240/75
USPC ........................................... 426/36
See application file for complete search history.

(56) References Cited

U.S. PATENT DOCUMENTS

| | | |
|---|---|---|
| 6,087,559 A | 7/2000 | Nichols |
| 7,582,743 B2 | 9/2009 | Horvath et al. |
| (Continued) | | |

FOREIGN PATENT DOCUMENTS

| | | |
|---|---|---|
| CN | 102965318 A | 3/2013 |
| WO | WO-03/102204 A2 | 12/2003 |
| WO | WO-2004/085607 A2 | 10/2004 |
| (Continued) | | |

OTHER PUBLICATIONS

L. Herve-Jimenez et al: "Postgenomic Analysis of *Streptococcus thermophilus* Cocultivated in Milk with *Lactobacillus delbrueckii* subsp. *bulgaricus*: Involvement of Nitrogen, Purine, and Iron Metabolism", Applied and Environmental Microbiology, vol. 75, No. 7, Apr. 1, 2009, pp. 2062-2073. (Year: 2009).*

(Continued)

*Primary Examiner* — Brent T O'Hern
(74) *Attorney, Agent, or Firm* — Foley & Lardner LLP

(57) ABSTRACT

The present invention relates to a bacterial cell with texturizing property, starter cultures comprising the cell, and dairy products manufactured using the bacterial cell.

15 Claims, 5 Drawing Sheets

Figure 2:
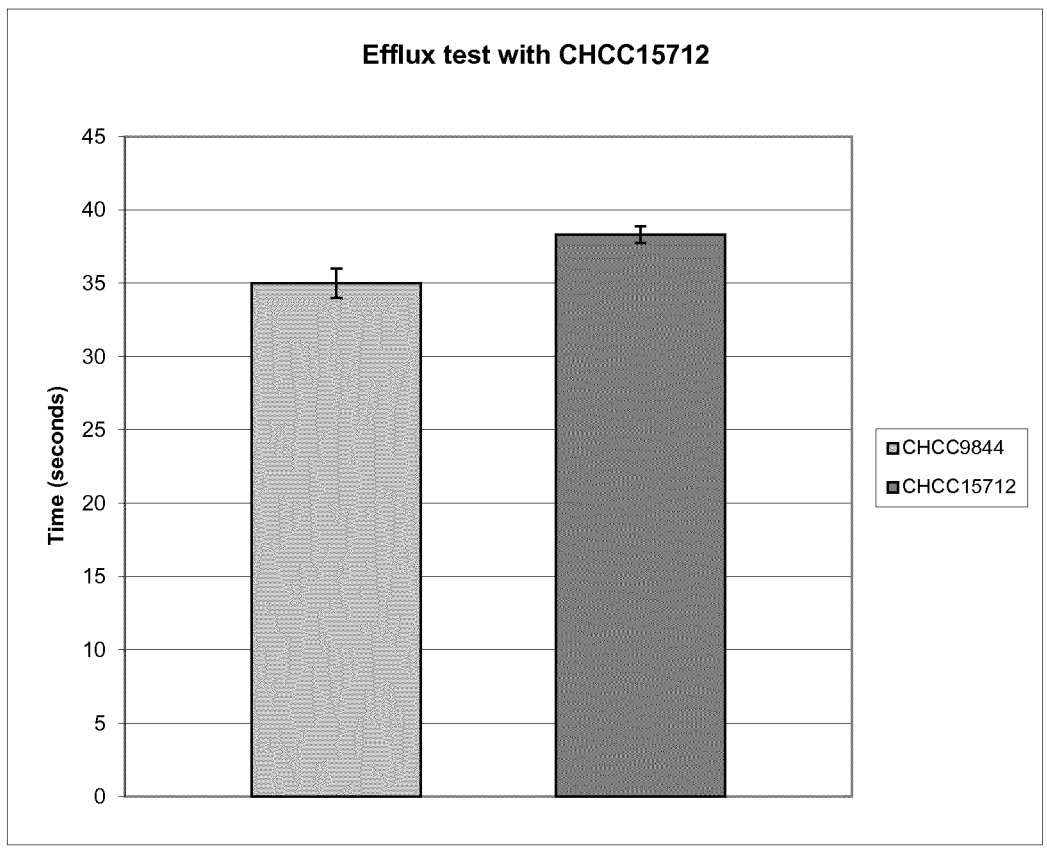

Specification includes a Sequence Listing.

(56) References Cited

U.S. PATENT DOCUMENTS

| | | |
|---|---|---|
| 9,453,231 B2 | 9/2016 | Kibenich et al. |
| 2004/0146983 A1 | 7/2004 | Caufield et al. |

FOREIGN PATENT DOCUMENTS

| | | |
|---|---|---|
| WO | WO-2011/026863 A1 | 3/2011 |
| WO | WO-2012/052557 A1 | 4/2012 |

OTHER PUBLICATIONS

Sieuwerts et al., Mixed-Culture Transcriptome Analysis Reveals the Molecular Basis of Mixed-Culture Growth in *Streptococcus thermophilus* and Lactobacillus bulgaricus' Appl Environ Microbiol. Dec. 2010; 76(23): 7775-7784. (Year: 2010).*

Bruno-Ba'rcena et al., Role of Antioxidant Enzymes in Bacterial Resistance to Organic Acids, Applied and Environmental Microbiology, May 2010, p. 2747-2753. (Year: 2010).*

31. Turner et al., Inactivation of an Iron Transporter in Lactococcus lactis Results in Resistance to Tellurite and Oxidative Stress, Applied and Environmental Microbiology, Oct. 2007, p. 6144-6149. (Year: 2007).*

Archibald et al., "Manganese: Its Acquisition by and Function in the Lactic Acid Bacteria," CRC Critical Reviews in Microbiology, (Jan. 1986), vol. 13, Issue 1, pp. 63-109, XP009146235.

Baichoo et al., "Global analysis of the Bacillus subtilis Fur regulon and the iron starvation stimulon," Molecular Microbiology (2002) 45(6), pp. 1613-1629.

Bruno-Barcena et al., "Role of Antioxidant Enzymes in Bacterial Resistance to Organic Acids," Applied and Environmental Microbiology, (May 2010) vol. 76, No. 9, pp. 2747-2753, XP055329035.

Garate et al., "Distribution of Fur family of transcriptional regulators in species belonging to the Lactobacillales order," (Apr. 2012) Retrieve from the Internet: URL:https:jjwww.researchgate.netjprofile/ Angelica Reyes-Jarajpublication/266159271 Distribution of Fur family of transcription al regulators Tn species belonging to the Lactobacillales orderjlinks/54c156a88cf2d03485c53693/Distribution-of-Fur-family-of-transcriptional-regulators-in-species-belonging-to-th [retrieved on Nov. 21, 2017] XP055427269.

Herve-Jimenez et al., "Postgenomic Analysis of *Streptococcus thermophilus* Cocultivated in Milk with *Lactobacillus delbrueckii* subsp. *bulgaricus*: Involvement of Nitrogen, Purine, and Iron Metabolism," Applied and Environmental Microbiology, (Apr. 2009), vol. 75, No. 7, pp. 2062-2073, XP055422417.

Kosikowski et al., "Cheese and Fermented Milk Foods," 3rd Ed., vol. I, Chapter 7: Fundamentals of Cheese Making and Ripening, pp. 109-126 (1997).

Lin et al., "Fur regulation of the capsular polysaccharide biosynthesis and iron-acquisition systems in Klebsiella pneumoniae CG43," Microbiology (2011) 157, pp. 419-429.

Saavedra et al., "EPS production during adaptation of Acidithibacillus ferrooxidans to high ferric ion concentration," Advanced Materials Research vol. 825 (2013) pp. 115-119.

Sieuwerts et al., "Mixed-Culture Transcriptome Analysis Reveals the Molecular Basis of Mixed-Culture Growth in *Streptococcus thermophilus* and Lactobacillus bulgaricus," Applied and Environmental Microbiology, (Dec. 2010) vol. 76, No. 23, pp. 7775-7784, XP055282830.

Skaar, "The Battle for Iron between Bacterial Pathogens and Their Vertebrate Hosts," PLoS Pathogens, (Aug. 2010) vol. 6, Issue 8, e1000949, pp. 1-4.

Turner et al., "Inactivation of an Iron Transporter in Lactococcus lactis Results in Resistance to Tellurite and Oxidative Stress," Applied and Environmental Microbiology, (Oct. 2007), vol. 73, No. 19, pp. 6144-6149, XP055427707.

Weinberg, "The Lactobacillus Naomaly: Total Iron Abstinence," Perspectives in Biology and Medicine, 40, 4, (Jul. 1997) pp. 578-583, XP009501662.

Yamamoto et al., "Regulation of the Intracellular Free Iron Pool by Dpr Provides Oxygen Tolerance to *Streptococcus mutans*," Journal of Bacteriology, vol. 186, No. 18, pp. 5997-6002, (Sep. 2004).

Zhang et al., "A Fur-like protein PerR regulates two oxidative stress response related operons dpr and metQIN in *Streptococcus suis*," BMC Mircrobiology, vol. 12. No. 85, pp. 1-12 (2012).

Bolotin et al., "Complete sequence and comparative genome analysis of the dairy bacterium *Streptococcus thermophilus*," Nature Biotechnology, vol. 22, No. 12, pp. 1554-1558 (Dec. 2004) (Published online Nov. 2004).

Van De Guchte et al., "The complete genome sequence of Lactobacillus bulgaricus reveals extensive ongoing reductive evolution," PNAS, vol. 103, No. 24, pp. 9274-9279 (Jun. 2006).

Wu et al., "Genomic insights into high exopolysaccharide-producing dairy starter bacterium *Streptococcus thermophilus* ASCC 1275," Scientific Reports, 4: 4974, pp. 1-8 (May 2014).

\* cited by examiner

| | |
|---|---|
| FURBOX Bacillus | GATAATGATAAT CATTATC |
| FURBOX S. gordonii | GCTATAGAAAAT GATAGTT |
| FURBOX CHCC9844 | TTTGAAAAAAAT GACAATT |

Fig. 1A

```
AAAAATATTT GGAAGAAGAA GACTTTTAAT AAATAGGTAA ATATCTGACA ATTTAAAGTT TAACTACTAA AAATGTGAAA GATAGTTCAC AATATAATGG
TTTTTATAAA CCTTCTTCTT CTGAAAATTA TTTATCCATT TATAGACTGT TAAATTTCAA ATTGATGATT TTACACTTT CTATCAAGTG TTATATTACC                              -10
AAAATGATAT AAATTAAATG ATTGATATCA TAATGAAAAC GTTTTTTTGT TTTTTTGA AAAAATGAC AATGAAATG AAATTGTATT AATGTAACA
TTTACTATA TTTAATTTAC TAACTATAGT ATTACTTTTG CAAAAAAACA AAAAAAACT TTTTTACTG TTACTTTAC TTTAACATAA TTACATTGT

AATAATGGG GAATACTTAA TTTTAATTTT TAGGAGAAT TTATATGAGT TCGCGTACGA ATCGTAAGCA AAAACGTACG GGTAATAGAT CATGGGGAT
TTATTACCC CTTATGAATT AAAATTAAAA ATCCTCTTA AATATACTCA AGCGCATGCT TAGCATTCGT TTTGCATGC CCATTATCTA GTACCCCCTA

GGTCAACGTT GGATTGACCA TTCTGTATGC TATTTAGCA TTGGTCTTAT AATTCACCAT GTTCAATTAT AATTTCCAAT CCTTTAGGTT TTTGAACATC
CCAGTTGCAA CCTAACTGGT AAGACATACG ATAAAATCGT AACCAGAATA ATAAGTGGTA CAAGTTAATA TTAAAGGATA GGAAATCCAA AAACTTGTAG

ATTATCACTA TTGGTTTGTT GGTAGTTCTT GCTATTAGGA TCTTCCTTCA GAAGACTAAG AAATCACCAC TAGTGACAAC GGTTGTAGTG GTTATCTTCT
TAATAGTGAT AACCAAACAA CCATCAAGAA CGATAATCGA AGAAGGAAGT CTTCTGATTC TTTAGTGGTG ATCACTGTTG CCAACATAAC CAATAGAAGA

CGCTAGTTTC TCTGGTTGGT ATTTTTGGTT TTAAACAAAT GATTGACATC ACTAACCGTA TGAATCAGAC GGCAGCATTT TCTGAAGTAG AAATAAGCAT
GCGATCAAAG AGACCAACCA TAAAAACCAA AATTTGTTTA CTAACTGTAG TGATTGGCAT ACTTAGTCTG CCGTCGTAAA AGACTTCATC TTTACTCGTA
```

RBS     Start codon     Fur box

Fig. 1B

BACTERIA

CROSS-REFERENCE TO RELATED APPLICATIONS

The present application is the U.S. National Stage of International Application PCT/EP2017/071352, filed Aug. 24, 2017, and claims priority to International Application No. PCT/DK2016/000031, filed Sep. 1, 2016.

SEQUENCE LISTING

The instant application contains a Sequence Listing which has been filed electronically in ASCII format and is hereby incorporated by reference in its entirety. Said ASCII copy, created on Apr. 18, 2019, is named 030427-0292_SL.txt and is 1,748 bytes in size.

FIELD OF INVENTION

The present invention relates to a bacterial cell with texturizing property, starter cultures comprising the cell, and dairy products manufactured using the bacterial cell.

BACKGROUND OF INVENTION

The food industry uses numerous bacteria, in particular lactic acid bacteria (LAB), in order to improve the taste and the texture of foods but also in order to extend the shelf life of these foods. In the case of the dairy industry, LAB are used extensively in order to bring about the acidification of milk (by fermentation) but also in order to texturize the product into which they are incorporated.

Among the LAB used in the food industry, there can be mentioned the genera *Streptococcus, Lactococcus, Lactobacillus, Leuconostoc, Pediococcus* and *Bifidobacterium*.

The LAB are used extensively alone or in combination with other bacteria for the production of food products, in particular fermented products. They are used in particular in the formulation of the starter cultures used for the production of fermented milks, for example yogurts.

Certain of them play a dominant role in the development of the texture of the fermented product. This characteristic is closely linked to the production of polysaccharides. Among the strains of *Streptococcus thermophilus* and *Lactobacillus bulgaricus* it is possible to distinguish texturizing and non-texturizing strains.

In order to meet the requirements of the industry, it has become necessary to propose novel texturizing strains of LAB, in particular of *Streptococcus thermophilus* and *Lactobacillus* species. One specific focus could be to reduce for example the amount of proteins or pectin (both improving texture) in dairy products, as these are both costly.

Thus the problem that the invention proposes to resolve is to provide a strain of lactic acid bacterium having good properties for texturizing food products, especially products where the texturizing strain of the lactic acid bacterium (such as *Streptococcus thermophilus*) is used together with a strain of a *Lactobacillus* species.

SUMMARY OF INVENTION

The present inventors have surprisingly found that the concentration of metal ions in lactic acid bacteria cells, or in starter cultures containing lactic acid bacteria cells, influence the formation of texture when such bacteria cells, or starter cultures, are used for the production of fermented milk.

In accordance with this surprising finding, the present invention relates to novel LAB strains with improved texturizing properties, and a method for producing such strains, and to fermented milk products made using such strains.

Thus, an aspect of the present invention relates to a composition of lactic acid bacteria that are able to texturize a milk substrate, said composition comprises lactic acid bacteria having a lowered intracellular concentration of metal ions, and/or said composition comprises a lowered amount of metal ions.

It is contemplated that such cells can be obtained in different ways, such as:

Alternative A): Genetically modification of the cell, so the cell will not take up metal ions, or only take up metal ions at a low rate, or so the cell will not be able to synthesize fully functional ion binding proteins, Alternative B): Growth of the cells in a growth medium without, or having a low concentration of metal ions, e.g. by addition of a metal ion chelating agent to the medium, or Alternative C): Isolation of mutant cells, e.g. obtained by mutagenization treatment (including treatment with a chemical mutagen, or UV light) of a mother cell.

Relating to alternative A), the present inventors describe the finding that mutants of texturizing LAB which are perturbed (such as decreased, suppressed) in their ion metabolism will give superior texture in a fermented milk product.

In a second aspect, the present invention relates to a method for increasing the viscosity of a dairy product fermented with LAB, said method comprises fermenting a milk substrate with reduced iron (esp. $Fe^{2+}$) and/or manganese (esp. $Mn^{2+}$) content, or fermenting a milk substrate where at least one of said metal ions are made partly or fully inaccessible for the LAB.

DETAILED DISCLOSURE

The present invention is based on the surprisingly finding that milk fermented with *S. thermophilus* strain CHCC15712—isolated as a mutant of the exopolysaccharide (EPS) producing strain *S. thermophilus* CHCC9844—showed increased shear stress as well as increased gel stiffness, two important rheology parameters which are believed to be related with texturing properties in yoghurt and yoghurt type products. Viscosity, measured by monitoring the efflux time from a volumetric pipette, was increased as well (see example 1).

The isolation and characterisation of EPS from CHCC9844 and CHCC15712 showed an increase of EPS production for CHCC15712 by 9% which correlates well with the viscosity increase (example 2).

Analyzing the mutant CHCC15712, the inventors surprisingly revealed that the cells contained an abnormal low concentration of $Fe^{2+}$ and other metal ions compared to CHCC9844.

The inventors investigated the possible mechanism underlying the surprising finding, and in the genome sequence of CHCC9844 they identified in the upstream region of the EpsA gene, a part of the CHCC9844 eps operon, a sequence which is highly homologous to the Fur (ferric uptake regulator) box, indicating that Fur is involved in the regulation of EPS expression of CHCC9844 (FIGS. 1A and 1B).

Without wishing to be bound to a specific theory or hypothesis, it is believed that EpsA expression is under control of Fur and de-repression of EpsA leads to increased EPS production and increased texture. Any mutant with impaired divalent metal uptake will therefore give increased texture, compared to a mother strain which has normal uptake.

By DNA array (expression microarray) analysis of CHCC15712 in comparison with CHCC9844 it was shown that a specific iron uptake gene cassette (Fat operon) was down regulated. The fatABC genes were about 4-fold lower expressed in CHCC15712 and fatD was 2-fold lower expressed compared to CHCC9844.

Investigations Relating to Alternative A) Above:

The inventors speculated that this down-regulation of the iron transporter will result in a reduced intracellular $Fe^{2+}$ or $Fe^{3+}$ concentration which again will lead to less binding of the Fur regulator to Fur boxes. Since Fur works as a repressor, genes under control of Fur are therefore de-repressed by reduced $Fe^{2+/3+}$ concentrations.

A down regulation of all other genes involved in uptake of iron, like e.g. the divalent metal ion ABC uptake system (NRAMP), would also lead to a lower intracellular iron concentration and, via Fur regulation, to increased texture.

The hypothesis was tested by making a genetically engineered mutant of CHCC9844 where the fur gene was inactivated. The effect on texture was measured using the pipette efflux test. The wt strain CHCC9844 had a pipette value of 24±1 s whereas the fur mutant KA509 measured 38±0 s corresponding to a 58% increase (example 3).

The effect of the fur inactivation on gene expression was also estimated using DNA microarrays. The genes fatABDC involved in iron uptake are known to be regulated by Fur. In KA509 these genes were down regulated 4-fold compared to the CHCC9844 wt strain. When KA509 was grown in presence of 10 mM $Fe^{2+}$ there was no substantial changes in expression of the fat gene cluster. Contrarily, when the mother strain CHCC9844 was grown in presence of iron, the fatC and fatD genes were induced 4-fold.

Investigations Relating to Alternative B) Above:

The hypothesis was tested further by performing milk acidification experiments in the presence of EDTA, a metal chelator. Addition of EDTA should reduce the amount of available iron and therefore result in de-repressing of EpsA resulting in increased texture. Indeed it was observed that the addition of 1 mM EDTA to milk increased the texture of milk fermented with CHCC15712 by 25% (example 5).

Investigations Relating to Alternative C) Above:

Based on the finding that mutants from CHCC9844 showed reduced expression of genes related to iron uptake, tellurite resistant mutants were isolated from CHCC9844.

The efflux time using the pipette test, and by this the viscosity, was increased for the tellurite resistant mutants. The highest increase was measured for mutant 9844-K2 with 47% (example 4).

With this experiment it was demonstrated that it is possible to increase the texturing properties of eps positive *S. thermophilus* strains further by the isolation of tellurite resistant mutants. The present invention also includes this embodiment.

Based on the above surprising findings, the present invention in a first aspect relates to a bacterium cell, such as lactic acid bacterium (LAB), which intracellularly contains less than 4200 ppm (parts per million, mg/Kg dry weight) in total of all divalent metal ions, such as less than 4100, less than 4000, 3000 or less than 2000 ppm. Interesting embodiments of such a bacterial cell are:

A LAB which contains less than 4200 ppm in total of $Fe^{2+}$, $Mg^{2+}$ and $Mn^{2+}$, such as less than 4100, less than 4000, less than 3000, less than 2000 or less than 1000 ppm.

A LAB which contains less than 4200 ppm of $Mg^{2+}$, such as less than 4100, less than 4000, less than 3000, less than 2000 or less than 1000 ppm.

A LAB which contains less than 10 ppm of $Fe^{2+}$, such as less than 9, less than 8, less than 6 or less than 3 ppm.

A LAB which contains less than 6 ppm of $Mn^{2+}$, such as less than 5.5, less than 5, less than 4 or less than 2 ppm.

A LAB which contains less than 16 ppm in total of $Fe^{2+}$ and $Mn^{2+}$, such as less than 15, less than 14, less than 10 or less than 7 ppm.

A LAB which in freeze dried form contains less than 2000 ppm of any divalent metal ion, esp. Mg.

A LAB which in freeze dried form contains less than 4000 ppm (w/w) divalent metal ions.

A LAB which in dried form contains less than 10 ppm (w/w) of iron, such as less than 9 ppm or less than 8.

A LAB which in freeze dried form contains less than 8 ppm (w/w) of iron.

The bacteria cells of the first aspect of the invention are able to texturize a milk substrate, when allowed to ferment a milk substrate. Thus, a further interesting embodiment relates to the lactic acid bacterium of the invention, which generates a viscosity greater than about 50 Pa·s (such as greater than 60 or 70 Pa·s) in milk, measured as shear stress after 16 hours of growth of the bacterium in 9.5% reconstituted skim milk at 37 degrees C., when the milk is inoculated with 10E8 CFU (colony forming units) per ml.

Further interesting embodiments are:

A lactic acid bacterium (LAB) which has a perturbed divalent metal ion metabolism (DMIM).

A LAB, which has a perturbed divalent metal ion metabolism (DMIM).

A LAB, wherein the perturbed DMIM is a decrease in the DMIM.

A LAB, wherein the perturbed DMIM is caused by a changed expression of the fur gene.

A LAB, wherein the perturbed DMIM is caused by a mutation in a gene related to the uptake of a divalent metal ion.

A LAB, wherein the perturbed DMIM is caused by reduced expression of an mntH gene.

A LAB, wherein the perturbed DMIM is caused by reduced expression of the fatc gene or of any other gene involved in the uptake of iron.

A LAB, wherein the perturbed DMIM is caused by that the bacterium is resistant to tellurite.

A LAB, wherein the divalent metal ion is selected from the group consisting of $Fe^{2+}$, $Mg^{2+}$, $Mn^{2+}$, $Te^{2+}$, $Ca^{2+}$, $Zn^{2+}$, $Co^{2+}$, $Ni^{2+}$ and $Cu^{2+}$.

A LAB, wherein the divalent metal ion is selected from the group consisting of $Fe^{2+}$, $Mg^{2+}$, and $Mn^{2+}$.

A LAB, wherein the divalent metal ion is $Fr^{2+}$.

A LAB, wherein the divalent metal ion is $Mn^{2+}$.

A LAB, which has been obtained by mutagenesis, by genetic engineering, and/or by growth in a medium having a concentration of divalent metal ions, (such as Fe) below 0.1% (w/v).

A LAB, which belong to a species selected from the group consisting of: *Streptococcus thermophilus* and *Lactobacillus bulgaricus*.

A LAB, which belong to the species *Streptococcus thermophilus*.

A LAB which is resistant to tellurite.

The strain *Streptococcus thermophilus* CHCC15712 (DSM25955), or a mutant or a variant of this strain.

In a second aspect, the present invention relates to a composition comprising a LAB of the first aspect.

In a third aspect, the present invention relates to composition comprising a LAB, said composition further comprises a metal ion chelator (such as EDTA or a siderophore or a ionophore), preferably in a concentration of 1 ppm or higher.

Interesting embodiments of the second and third aspects are:

A composition which is a starter culture.

A composition which comprises at least 10E9 CFU of a LAB of the invention.

A composition which comprises at least 10E11 (10exp11) CFU of a LAB of the invention.

A composition which comprises from 10E10 CFU to 10E14 CFU of a LAB of the invention.

A composition which is usable as a starter culture, and/or is in frozen or dry form, such as freeze-dried.

A composition which contains less than 4200 ppm in total of all divalent metal ions, such as less than 4100, less than 4000, less than 3000, less than 2000 or less than 1000 ppm.

A composition which contains less than 4200 ppm in total of $Fe^{2+}$, $Mg^{2+}$, and $Mn^{2+}$, such as less than 4100, less than 4000, less than 3000, less than 2000 or less than 1000 ppm.

A composition which contains less than 4200 ppm of $Mg^{2+}$, such as less than 4100, less than 4000, less than 3000, less than 2000 or less than 1000 ppm.

A composition which contains less than 10 ppm of $Fe^{2+}$, such as less than 8, less than 6 or less than 3 ppm.

A composition which contains less than 6 ppm of $Mn^{2+}$, such as less than 5, less than 4 or less than 2 ppm.

A composition which contains less than 16 ppm in total of $Fe^{2+}$ and $Mn^{2+}$, such as less than 15, less than 14, less than 10 or less than 7 ppm.

A composition which contains 2 different LAB strains.

A composition wherein the 2 different LAB strains belong to different species.

In a fourth aspect, the present invention relates to a method for producing a fermented milk product/dairy product, comprising fermenting a milk substrate with a LAB of the invention, a strain/cell of the invention, or a composition of the invention.

In a sixth aspect, the present invention relates to a dairy product, such as a fermented milk product (e.g. yoghurt or buttermilk) or a cheese (e.g. fresh cheese or pasta filata), obtainable by the method of the invention. The dairy product optionally comprises an ingredient selected from the group consisting of: a fruit concentrate, a syrup, a probiotic bacterial culture, a coloring agent, a thickening agent, a flavoring agent, and a preserving agent; and/or which optionally is in the form of a stirred type product, a set type product, or a drinkable product.

In a yet an aspect, the present invention relates to a method for producing a LAB strain that provides texture when inoculated into a milk substrate, comprising: i) Providing a LAB strain (the mother strain), ii) Introducing a mutation in the fur gene of the mother strain, i.e., by genetic engineering or mutagenization, and iii) Screening for mutants which have improved texturizing properties compared to the mother strain.

Other interesting aspects (claim aspects) of the invention are listed below:

1. A lactic acid bacterium (LAB) which contains less than 10 ppm (parts per million, mg/Kg dry weight) of iron ions (e.g. $Fe^{2+}$), such as less than 9, less than 8 ppm, less than 6 or less than 3 ppm.
2. A LAB which contains less than 6 ppm (parts per million, mg/Kg dry weight) of Manganese ions (e.g. $Mn^{2+}$), such as less than 5.5, less than 5.2 ppm, less than 5 ppm, less than 4 or less than 2 ppm.
3. The LAB of any preceding claim aspect which contains less than 16 ppm in total of $Fe^{2+}$ and $Mn^{2+}$, such as less than 15, less than 14 ppm, less than 13 ppm, less than 10 or less than 7 ppm.
4. The lactic acid bacterium (LAB) of any preceding claim aspect, which has a perturbed divalent metal ion metabolism (DMIM).
5. A lactic acid bacterium (LAB) which has a perturbed divalent metal ion metabolism (DMIM).
6. The LAB of any preceding claim aspect, wherein the perturbed DMIM is a decreased DMIM.
7. The LAB of any preceding claim aspect, wherein the perturbed DMIM is caused by a changed expression of the fur gene, such as (partly or full) inactivation of the gene, deletion of the gene or parts thereof and/or insertion of additional DNA into the gene.
8. The LAB of any preceding claim aspect, wherein the perturbed DMIM is caused by a mutation in a gene related to the uptake of a divalent metal ion, such as a knock-out mutation.
9. The LAB of any preceding claim aspect, wherein the perturbed DMIM is caused by reduced expression of an mntH gene.
10. The LAB of any preceding claim aspect, wherein the perturbed DMIM is caused by reduced expression of the fatc gene or of any other gene involved in the uptake of iron.
11. The LAB of any preceding claim aspect, wherein the perturbed DMIM is caused by that the bacterium is resistant to tellurite.
12. The LAB of any preceding claim aspect, wherein the divalent metal ion is selected from the group consisting of $Fe^{2+}$, $Mg^{2+}$, and $Mn^{2+}$, preferably the group $Fe^{2+}$, and $Mg^{2+}$.
13. The LAB of any preceding claim aspect, wherein the divalent metal ion is $Fe^{2+}$.
14. The LAB of any preceding claim aspect, wherein the divalent metal ion is $Mn^{2+}$.
15. The LAB of any preceding claim aspect, which has been obtained by mutagenesis, and/or by genetic engineering.
16. The LAB of any preceding claim aspect, which has been obtained by growth in a medium having a concentration of divalent metal ions, selected from the group consisting of $Fe^{2+}$ and $Mn^{2+}$ below 0.25 microgram/gram, such as below 0.2 µg/g.
17. The LAB of any preceding claim aspect, which belong to the species *Lactobacillus bulgaricus*.
18. The LAB of any preceding claim aspect, which belong to the species *Streptococcus thermophilus*.
19. The strain *Streptococcus thermophilus* CHCC15712 (DSM25955), or a mutant or a variant of this strain, such as a mutant or variant with improved EPS production.
20. The LAB of any preceding claim aspect, which is resistant to tellurite.
21. The LAB of any preceding claim aspect, which generates a viscosity greater than about 50 Pa·s (such as greater than 60 or 70 Pa·s) in milk, measured as shear stress after 16 hours of growth of the bacterium in 9.5% reconstituted skim milk at 37 degrees C., when the milk is inoculated with 10E8 CFU per ml.

22. A composition comprising a LAB (lactic acid bacterium) of any of the preceding claim aspects.

23. The composition of the preceding claim aspect, which is a starter culture.

24. A composition comprising a LAB, said composition further comprises a metal ion chelator, (such as EDTA), preferably in a concentration of 1 ppm or higher.

25. The composition of any preceding claim aspect, which comprises at least 10E9 CFU (cell forming units) of the LAB per mg.

26. The composition of any preceding claim aspect, which comprises at least 10E11 CFU of the LAB per mg.

27. The composition of the preceding claim aspect, which comprises from 10E10 CFU to 10E14 CFU of the LAB per mg.

28. The composition of any preceding claim aspect, which is in frozen or dry form, such as freeze-dried.

29. The composition of any preceding claim aspect, which contains less than 10 ppm of $Fe^{2+}$, such as less than 9.5, less than 9 ppm, less than 8 ppm, less than 6 or less than 3 ppm.

30. The composition of any preceding claim aspect, which contains less than 6 ppm of $Mn^{2+}$, such as less than 5.5, less than 5.2 ppm, less than 5 ppm, less than 4 or less than 2 ppm.

31. The composition of any preceding claim aspect, which contains less than 16 ppm in total of $Fe^{2+}$ and $Mn^{2+}$, such as less than 15, less than 14 ppm, less than 13 ppm, less than 10 or less than 7 ppm.

32. The composition of any preceding claim aspect, which contains at least 2 different LAB strains, such as at least 3, at least 5 or at least 10.

33. The composition of the preceding claim aspect, wherein at least 2 different LAB strains belong to different species.

34. A method for producing a dairy product (such as fermented milk (e.g. yoghurt) or cheese e.g. pasta filata or fresh cheese), comprising fermenting a milk substrate with a LAB of any preceding claim aspect, a strain of any preceding claim aspect, or a composition of any preceding claim aspect.

35. A method for producing a dairy product (such as fermented milk (e.g. yoghurt) or cheese e.g. pasta filata or fresh cheese), said method comprising fermenting a milk substrate having a $Fe^{2+}$ concentration below 0.25 µg/g (such as below 0.20 or below 0.15 µg/g) with a LAB, such as a LAB of any preceding claim aspect.

36. A method for producing a dairy product (such as fermented milk (e.g. yoghurt) or cheese), said method comprising fermenting a milk substrate having a $Mn^{2+}$ concentration 0.025 µg/g (such as below 0.020 or below 0.015 µg/g) with a LAB, such as a LAB of any preceding claim aspect.

37. A method for producing a dairy product (such as fermented milk (e.g. yoghurt) or cheese e.g. pasta filata or fresh cheese), comprising fermenting a milk substrate with a LAB which does not contain an active fur protein.

38. The method of any preceding claim aspect, wherein the LAB is a strain of *Streptococcus thermophilus*

39. The method of any preceding claim aspect, wherein the LAB is a strain of *Lactobacillus bulgaricus*

40. A dairy product, such as a fermented milk product (such as fermented milk (e.g. yoghurt) or cheese e.g. pasta filata or fresh cheese), obtainable by the method of any preceding claim aspect.

41. A dairy product of the preceding claim aspect, which optionally comprises an ingredient selected from the group consisting of: a fruit concentrate, a syrup, a probiotic bacterial culture, a coloring agent, a thickening agent, a flavoring agent, and a preserving agent;

and/or which optionally is in the form of a stirred type product, a set type product, or a drinkable product.

45. A method for producing a LAB strain that provides texture (or provides increased texture compared to the mother strain) when inoculated into a milk substrate, comprising:

Introducing a mutation in the fur gene of a LAB strain (mother strain), i.e., by genetic engineering or mutagenization, and Screening for mutants which has improved texturizing properties compared to the mother strain.

46. A method for improving the EPS production of a LAB strain (which is able to produce EPS), said method comprises: Removal of $Fe^{2+}$ ions from the medium (e.g., production medium or milk substrate) before, during or after inoculation with the strain, such as by addition of a metal chelator.

47. The method of the preceding claim aspect, wherein the resulting medium has a concentration of $Fe^{2+}$ ions below having a $Fe^{2+}$ concentration below 0.25 µg/g (such as below 0.20 or below 0.15 µg/g).

48. The method of any preceding claim aspect for improving the EPS production of a LAB strain, said method further comprises: Removal of $Mn^{2+}$ ions from the medium before, during or after inoculation with the strain.

49. The method of the preceding claim aspect for improving the EPS production of a LAB strain, wherein the resulting medium has a concentration has a $Mn^{2+}$ concentration below 0.025 µg/g (such as below 0.020 or below 0.015 µg/g).

50. The method any the preceding claim aspect, wherein the growth is carried out for at least hours.

51. A method for production of a LAB strain (which is able to produce EPS), said method comprises: Inactivation (partly or fully) of the fur gene.

Definitions

As used herein, the term "lactic acid bacterium" (short LAB) designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as culture in food fermentations alone or in combination with other lactic acid bacteria. Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters". Some dairies also employ "bulk starters" where the culture is propagated onsite before inoculation into for example milk.

In the present context, the term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder. Preferably, at least part of the protein in the milk substrate is proteins naturally occurring in milk, such as casein or whey protein. However, part of the protein may be proteins which are not naturally occurring in milk. Prior to fermentation, the milk substrate may be homogenized and pasteurized according to methods known in the art.

The term "milk" is to be understood as the lacteal secretion obtained by milking any mammal, such as cows, sheep, goats, buffaloes or camels. In a preferred embodiment, the milk is cow's milk. The term milk also comprises milk made of plant materials, such as soy milk. Optionally the milk is acidified, e.g. by addition of an acid (such as citric, acetic or lactic acid), or mixed, e.g. with water. The milk may be raw or processed, e.g. by filtering, sterilizing, pasteurizing, homogenizing etc., or it may be reconstituted dried milk. An important example of "bovine milk" according to the present invention is pasteurized cow's milk. It is understood that the milk may be acidified, mixed or processed before, during and/or after the inoculation with bacteria.

Cow milk contains iron in a concentration about 0.03 mg per 100 g=0.3 µg/g=0.3 ppm Cow milk contains manganese in a concentration about 0.03 µg/g=0.03 ppm In the present context, the term "mutant" should be understood as a strain derived from a strain of the invention by means of e.g. genetic engineering, radiation and/or chemical treatment, and/or selection, adaptation, screening, etc. The term also includes mutants with improved or altered phage resistance, e.g. phage hardened mutants. It is preferred that the mutant is a functionally equivalent mutant, e.g. a mutant that has substantially the same, or improved, properties (e.g. regarding yield, viscosity, gel stiffness, mouth coating, flavor, post acidification, acidification speed, and/or phage robustness) as the mother strain. In the present context a mutant of the invention is preferable a mutant with same or improved properties with respect to EPS production, and/or for generating viscosity when a milk substrate is fermented. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. The term mutant also includes a tellurite resistant mutant. By the term tellurite resistant mutant is understood a mutant which is able to grow (form a colony) on M17 agar plates containing 0.1 mM $K_2TeO_3$.

A mutant may have been subjected to several mutagenization treatments (a single treatment should be understood one mutagenisation step followed by a screening/selection step), but it is presently preferred that no more than 1000, no more than 100, no more than 20, no more than 10, or no more than 5, treatments are carried out. In a presently preferred mutant, less than 5%, or less than 1% or even less than 0.1% of the nucleotides in the bacterial genome have been changed (such as by replacement, insertion, deletion or a combination thereof) compared to the mother strain.

In the present context, the term "variant" should be understood as a strain which is functionally equivalent to a strain of the invention, e.g. having substantially the same, or improved, properties e.g. regarding viscosity, gel stiffness, mouth coating, flavor, post acidification, acidification speed, and/or phage robustness). Such variants, which may be identified using appropriate screening techniques, are a part of the present invention.

By inactivation of a gene is meant that the gene (including promotor and other regulatory regions) is amended in such a way that the gene or its product loses its activity (partly or fully). Inactivation can, for instance, be deletion (partly or fully) of the gene, mutation of the gene (e.g., by genetic engineering or mutagenisis), provision of knock-out mutants, introduction of frame shift, insertion of e.g. stop codons, etc.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

EXPERIMENTAL

Example 1: Isolation of a *Streptococcus Thermophilus* Mutant with a Perturbed Iron Metabolism by Conventional Mutagenization

*S. thermophilus* CHCC15712 was isolated as a mutant of the exopolysaccharide producing strain *S. thermophilus* CHCC9844. Milk fermented with CHCC15712 showed increased shear stress as well as increased gel stiffness, two important rheology parameters which are believed to be related with texturing properties in yoghurt type products. Viscosity, measured by monitoring the efflux time from a volumetric pipette was increased as well.

Viscosity is measured by monitoring the efflux time from a 25 ml volumetric pipette, which has been filled with 25 ml of a fermented milk prepared by 16 hours of growth of the bacterium in 9.5% reconstituted skim milk at 37 degrees C., when the milk is inoculated with 10E8 CFU per ml.

The rheological properties of the sample were assessed on a rheometer (StressTech, Reologica Instruments, Sweden) equipped with a C25 coaxial measuring system. The viscometry test was made with shear rates varying from 0.27 to 300 1/s in 21 steps. Shear rates were increased and then decreased and the upward and downward curves of shear stress and apparent viscosity were recorded. Delay and integration times were 5 s and 10 s, respectively. For further analysis, shear stress at 300 s-1 was chosen.

The rheometer results showed that CHCC15712 had shear stress and gel stiffness increased by 20% compared to CHCC9844.

Viscosity was also measured by calculating the efflux time from a 25 ml volumetric pipette. For CHCC15712 an increase of viscosity by 9% was measured compared to the wild type strain CHCC9844 (see FIG. 2). The efflux time was increased from 35 to 38 seconds which relates to a 9% viscosity increase.

Example 2: Production of Exopolysaccharides in M17 Broth

The two strains CHCC9844 and CHCC15712 were grown at 37° C. in M17 broth with 1% lactose for 16 hours. The cells were removed by centrifugation and EPS was extracted from the supernatant by precipitating proteins with 96% trichloroacetic acid solution (TCA), and afterwards precipitating EPS with 96% ethanol. The EPS samples were then dialyzed against Milli Q-water at 4° C. for at least 24 hours (Slide-A-lyzer dialysis cassette, 0.5-3 ml, MWCO 10000, Thermo scientific). EPS was then hydrolysed with 4M TFA (trifluoroacetic acid) and analysed for composition and amount of monosaccharides by HPLC.

Figure 3:
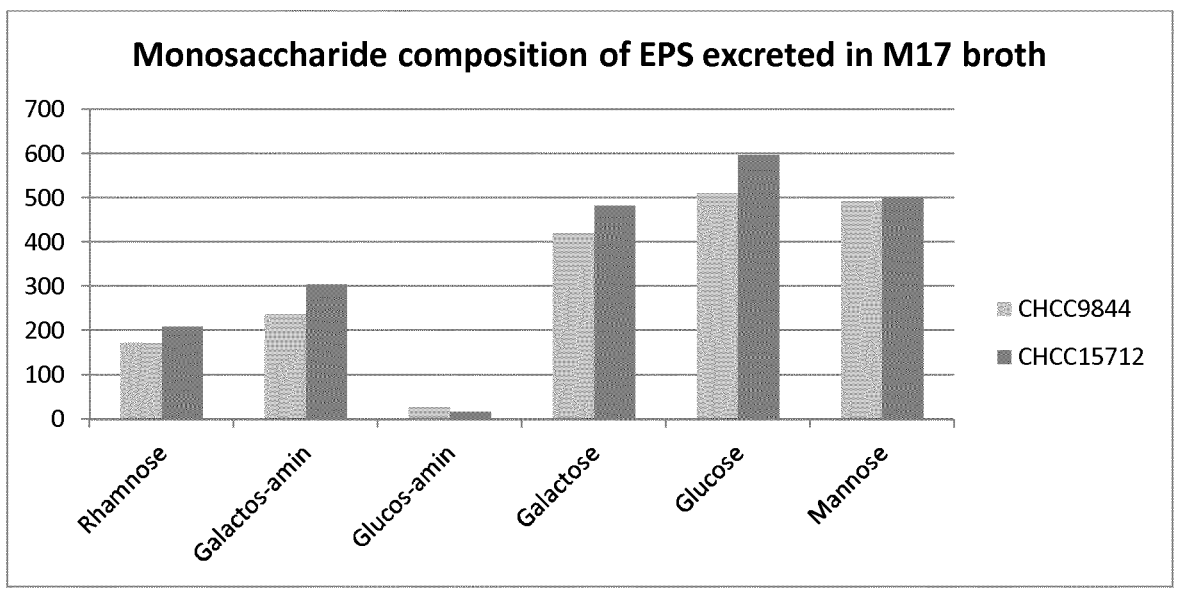

The HPLC analysis revealed the presence of rhamnose, galactosamine, galactose, glucose, and mannose in the EPS of CHCC9844 and CHCC15712 (see FIG. 3). The concentration of the carbohydrates rhamnose, galactosamine, galactose and glucose appeared to be increased. In total there was an increase of EPS carbohydrates by 13% (from 1868 ppm to 2114 ppm). This number relates good to the increase of viscosity measured for CHCC15712 (example 1).

strain CHCC9844 was grown in the presence of iron, the fatC and fatD genes were induced 4-fold.

Example 4: Isolation of Tellurite Resistant Mutants from *S. thermophilus* CHCC9844 with Increased Viscosity Parameters Based on our finding that mutants from CHCC9844 showed reduced expression of genes related to iron uptake, tellurite resistant mutants were isolated from CHCC9844.

The mutants were directly screened on M17 agar plates containing 0.1 mM $K_2TeO_3$. Four mutants were purified demonstrating a stable tellurite resistant phenotype. The four CHCC9844 mutants were inoculated from an M17 overnight culture containing 0.1 mM $K_2TeO_3$ 1% in milk, and incubated at 37° C. for 24 hours. The viscosity of the fermented milk was then determined by measuring efflux time from a 25 ml pipette. The longer the efflux time the higher is the viscosity of the test medium: for each strain the efflux time is indicated as an average of three measurements (see FIG. 5).

The efflux time, and by this the viscosity, was increased for the four tellurite resistant mutants. The highest increase was measured for mutant 9844-K2 with 47%.

With this experiment it was demonstrated that it is possible to increase the texturing properties of eps positive *S. thermophilus* strains further by the isolation of tellurite resistant mutants.

Example 5: The Effect of the Addition of a Metal Chelator (EDTA) on Texture

The hypothesis that a reduced iron concentration modulates viscosity was tested by performing milk acidification in the presence of EDTA, a metal chelator. Addition of EDTA should reduce the amount of available iron and therefore

|  | Rhamnose | Galactosamin | Glucosamin | Galactose | Glucose | Mannose | Total |
|---|---|---|---|---|---|---|---|
| CHCC9844 | 174 | 238 | 28.7 | 421.4 | 511.35 | 495 | 1868 |
| CHCC15712 | 210 | 305 | 17 | 482 | 597 | 502 | 2114 |

Example 3: GMO Fur Inactivation Mutant with Increased Texture Formation

Strain KA509 is a mutant of CHCC9844 where the fur gene was genetically inactivated. This was done by single crossover of a plasmid vector harbouring an internal fragment containing bases 2-385 of the CHCC9844 fur gene. The resulting mutant has the vector inserted after the first nucleotide of the 485 bp long fur CDS (codon sequence). This results in disruption of the gene which is hence rendered inactive. Correct insertion was checked by PCR using one primer placed in the vector and one placed in the fur gene downstream of the internal fragment.

Figure 4:
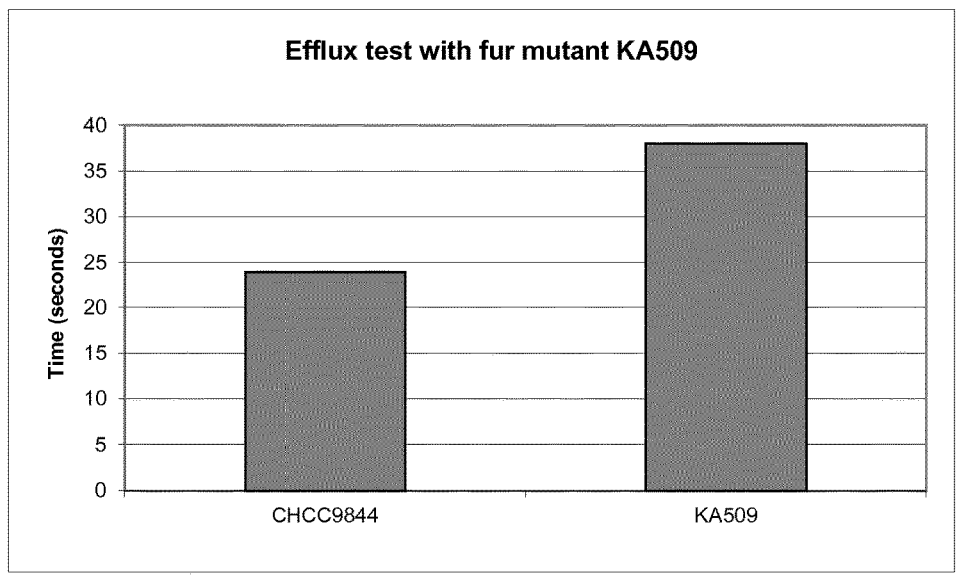

The effect on texture was checked using the pipette efflux test. The wt strain CHCC9844 had a pipette value of 24±1 s whereas the fur mutant measured 38±0 s corresponding to 58% increase (FIG. 4).

Figure 6:
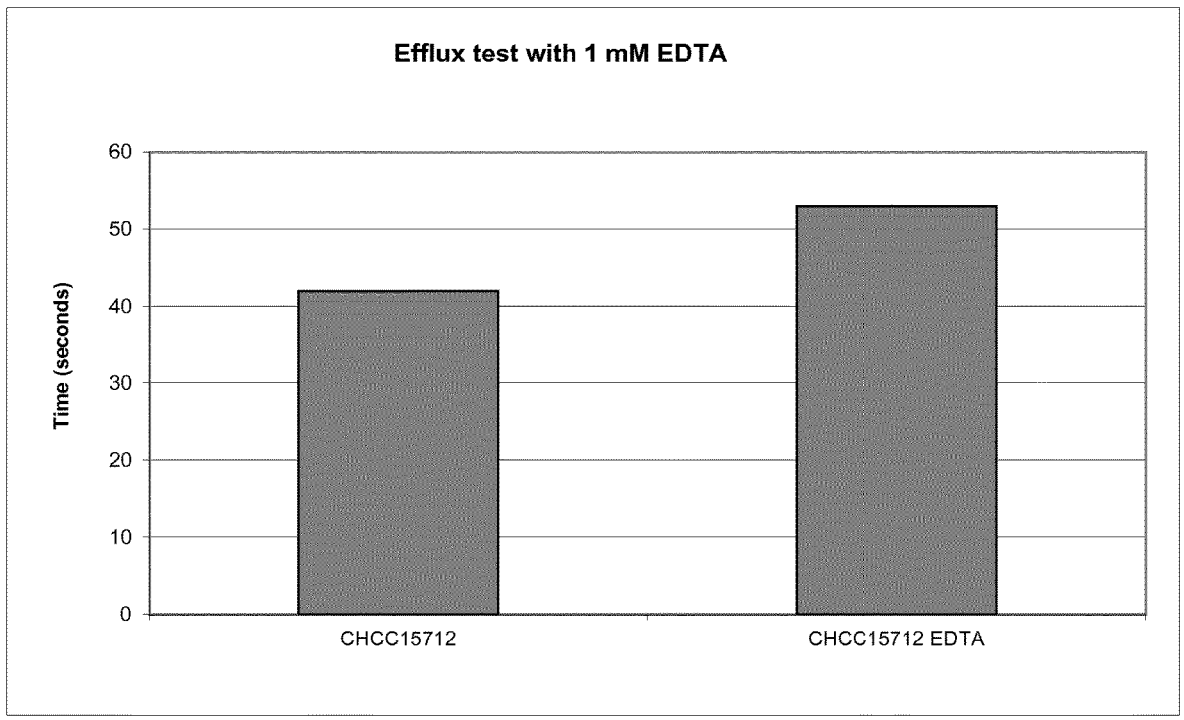

The effect of the fur inactivation on gene expression was also estimated using DNA microarrays. In KA509 the genes fatABDC were down regulated 4-fold compared to the CHCC9844 wt strain. When KA509 was grown in presence of 10 mM $Fe^{2+}$ there was no substantial changes in expression of the fat gene cluster. Contrarily, when the mother result in a de-repressing of EpsA resulting in increased texture. Indeed it was observed that the addition of 1 mM EDTA to milk increased the texture of CHCC15712 by 25% (FIG. 6).

Example 6: Method for Measuring the Content of Divalent Metal Ions

Strains of *Streptococcus thermophilus* without a perturbed divalent ion metabolism have been analysed for content of intracellular divalent ion concentrations.

For determination of intracellular ion concentration cells were grown over night in M17-2% lactose.

After centrifugation of 50 ml for 10 min at 5000 rpm, the cells were washed with 50 ml M17-2% lactose medium. All tubes were centrifuged at 5000 rpm for 10 minutes, supernatant discarded, and cells were then washed with 5 ml PBS buffer (treated o/n with Chelex, 10 g in 1 Litre buffer). All tubes were centrifuged for 10 minutes at 5000 rpm, and then washed with 5 ml PBS buffer, centrifuged for 10 minutes at 5000 rpm and washed/resuspended in 1 ml PBS buffer and transferred to a 2 ml Eppendorf tube. The tubes were then centrifuged for 15 minutes at 15.000×g and the supernatants were discarded as much as possible.

The tubes were dried in a speedvac o/n at RT (room temperature). All pellets were weighed.

After weighing, the pellets were solubilized by the addition of 200 μL concentrated (65%) Nitric acid with 0.1% Triton X-100, shaking the tubes at 95° C. for 10 minutes and afterwards vortexing each tube for 20 seconds.

After vortexing, the tubes were centrifuged at 15.000×g for 5 minutes and the supernatant was taken off in a new tube.

Metal ion concentration of the samples was determined by ICP-MS (Inductively Coupled Plasma Mass Spectrometry).

Figure 7A:
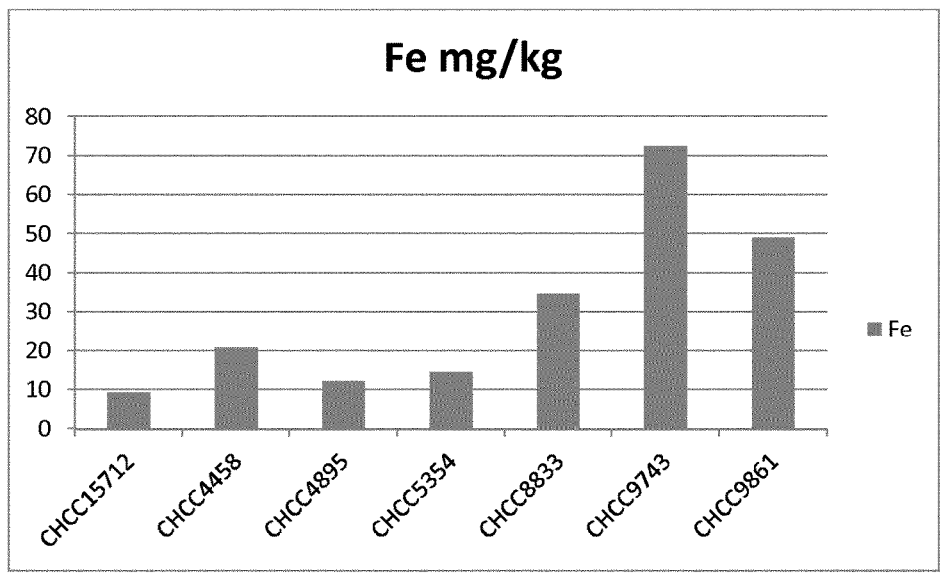
Figure 7B:
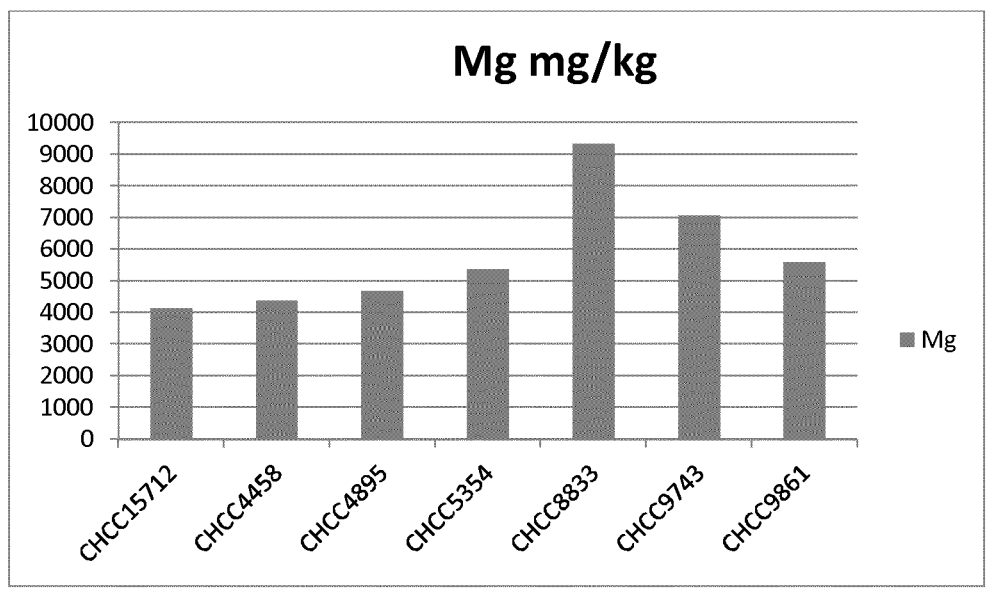
Figure 7C:
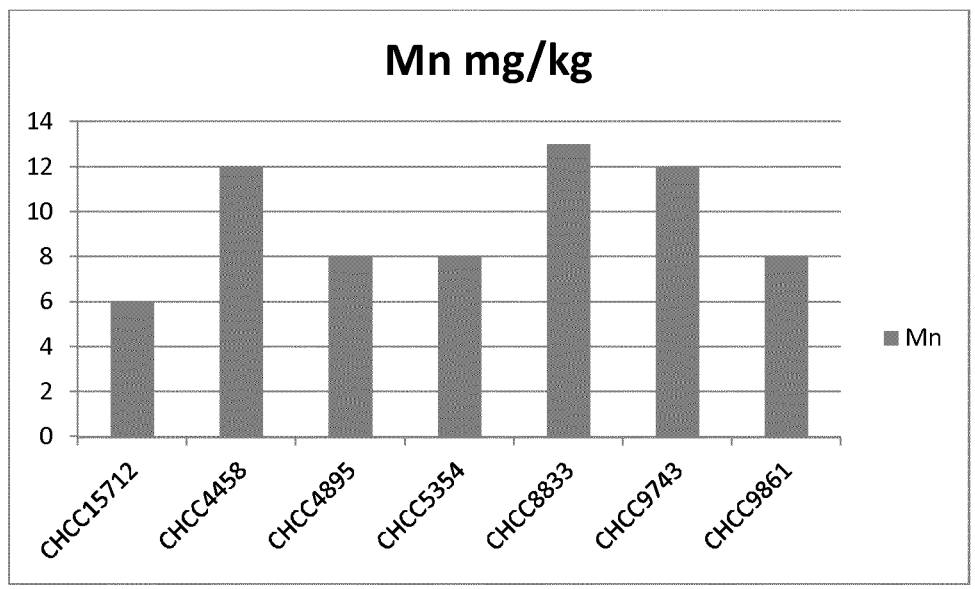

The results (see FIGS. 7a, 7b and 7c, showing results for strains CHCC15712, CHCC4458, CHCC4895, CHCC5354, CHCC8833, CHCC9743, and CHCC 9861) are expressed as ion concentration in mg per kg of dry weight of cells. Thus, in the present context, the term ppm (parts per million), should be understood as mg ion measured per Kg dry weight of cell mass.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

DRAWING

FIG. 1a depicts the alignment of Fur boxes from *Bacillus*, *Streptococcus gordonii* and CHCC9844. Nucleotides found in all three strains are coloured red, those shared between *Bacillus* and CHCC9844 are green, those shared between CHCC9844 and *S. gordonii* are blue. FIG. 1a discloses SEQ ID NOS 1-3, respectively, in order of appearance.

FIG. 1b depicts the promoter regions and first part of epsA gene in *S. thermophilus* CHCC9844. The postulated fur box is coloured blue. Other features of the promoter region are indicated on the figure. FIG. 1b discloses SEQ ID NO: 4.

FIG. 2 depicts a viscosity test with texturing mutant CHCC15712. Viscosity was measured by calculating the efflux time from a 25 ml volumetric pipette. The graph shows the average from three measurements.

FIG. 3 depicts the monosaccharide composition of exopolysaccharide excreted in M17 broth. The concentration of the single monosaccharides is indicated in ppm.

FIG. 4 depicts a viscosity test with fur mutant KA 509. Viscosity was measured by calculating the efflux time from a 25 ml volumetric pipette. The graph shows the average from three measurements.

Figure 5:
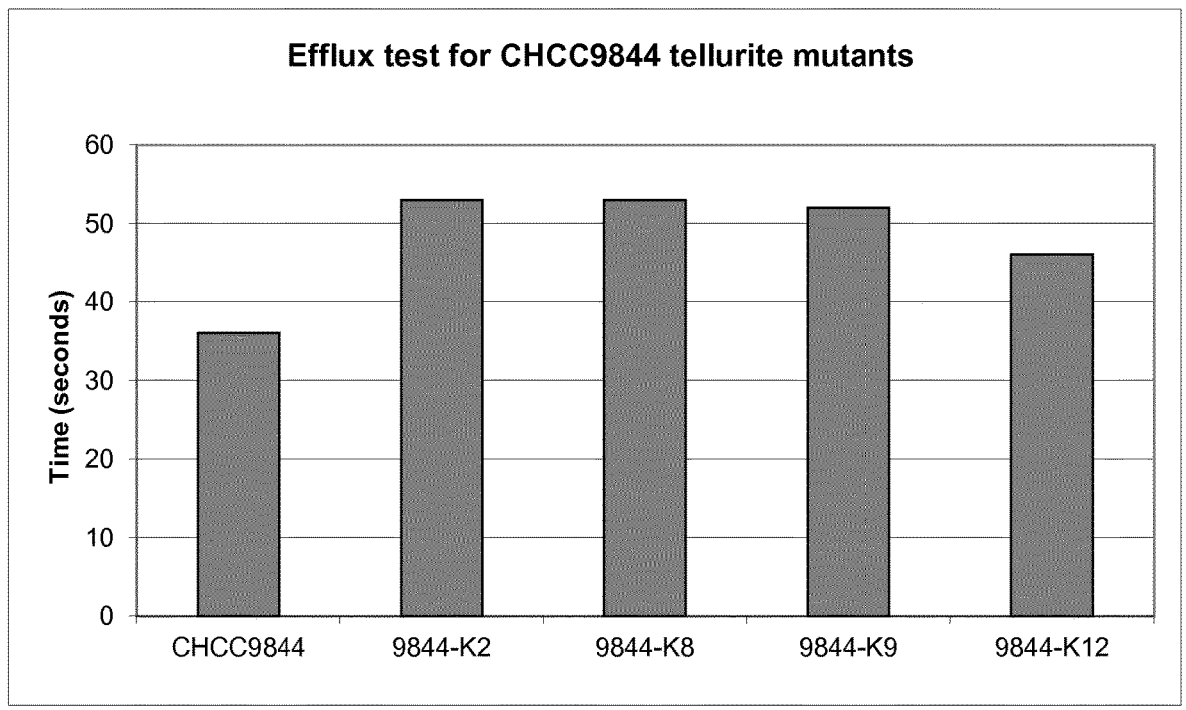

FIG. 5 depicts a viscosity test with four tellurite resistant mutants from CHCC9844. Viscosity was measured by calculating the efflux time in seconds from a 25 ml volumetric pipette. The graph shows the average from three measurements.

FIG. 6 depicts a viscosity test in milk with and without 1 mM EDTA. Viscosity was measured by calculating the efflux time in seconds from a 25 ml volumetric pipette. The graph shows the average from three measurements.

FIGS. 7a, 7b and 7c depict the intracellular concentrations of Fe, Mg, and Mn, resp.

DEPOSITS and EXPERT SOLUTION

The strain *Streptococcus thermophilus* CHCC15712 was deposited at DSMZ (Deutsche Sammlung von Mikroorganismen and Zellkulturen GmbH, Inhoffenstr. 7B, D-38124 Braunschweig, Germany) under the accession number DSM25955, on Apr. 27, 2012.

CHCC4895 was deposited with DSMZ under the accession no. DSM19242, on 29 Mar. 2007

CHCC8833 was deposited with DSMZ under the accession no. DSM17876, on 11 Jan. 2006.

The deposits were made according to the Budapest treaty on the international recognition of the deposit of microorganisms for the purposes of patent procedure.

The Applicant requests that a sample of the deposited microorganism should be made available only to an expert approved by the Applicant.

REFERENCES

Lin et al., Microbiology (2011), 157, 419-429.
E. P. Skaar, PLoS Pathog. (2010) August 12; 6(8):e1000949.
Baichoo et al., Molecular Microbiology (2002) 45 (6), 1613-1629.
Kosikowski, F. V. and Mistry, V. V., "Cheese and Fermented Milk Foods", 1997, 3rd Ed. F. V. Kosikowski, L.L.C. Westport, Conn.
Albert Saavedra et al., 2013, Advanced Materials Research, 825, 115

All references cited in this patent document are hereby incorporated herein in their entirety by reference.

The invention claimed is:

1. A method for increasing viscosity in a fermented milk product, comprising inoculating and fermenting a milk substrate with a mutant lactic acid bacterium (LAB) exhibiting one or more properties selected from:

(a) containing from 0 to less than 10 parts per million (ppm, mg/kg dry weight) of $Fe^{2+}$ ions;

(b) containing from 0 to less than 6 ppm of $Mn^{2+}$ ions;

(c) containing from 0 to less than 16 ppm in total of $Fe^{2+}$ ions and $Mn^{2+}$ ions;

(d) carrying a mutation in a gene related to the uptake of a divalent metal ion;

(e) having a changed fur gene expression caused by one or more of: a mutation that causes partial or full inactivation of the fur gene, a mutation that causes partial or full deletion of the fur gene, and a mutation that causes insertion of DNA into the fur gene;

(f) having reduced mnth gene expression caused by one or more of: a mutation that causes partial or full inactivation of the mnth gene, a mutation that causes partial or full deletion of the mnth gene, and a mutation that causes insertion of DNA into the mnth gene;

(g) having reduced fatc gene expression caused by one or more of: a mutation that causes partial or full inactivation of the fatc gene, a mutation that causes partial or full deletion of the fatc gene, and a mutation that causes insertion of DNA into the fatc gene; and (h) being resistant to tellurite, as determined by an ability to form a colony on M17 agar plates containing 0.1 mM $K_2TeO_3$, wherein the mutant LAB generates a viscosity in milk greater than about 50 Pa·s, measured as shear stress, after inoculating 9.5% reconstituted skim milk with $10^8$ CFU/ml milk of the mutant LAB and fermenting for 16 hours at 37° C.

2. The method of claim 1, wherein the mutant LAB exhibits one or more properties selected from:

(a) containing from 0 to less than 10 parts per million (ppm, mg/kg dry weight) of $Fe^{2+}$ ions;

(b) containing from 0 to less than 6 ppm of $Mn^{2+}$ ions; and (c) containing from 0 to less than 16 ppm in total of $Fe^{2+}$ ions and $Mn^{2+}$ ions.

3. The method of claim 1, wherein the mutant LAB exhibits one or more properties selected from:

(d) carrying a mutation in a gene related to the uptake of a divalent metal ion;

(e) having a changed fur gene expression caused by one or more of: a mutation that causes partial or full inactivation of the fur gene, a mutation that causes partial or full deletion of the fur gene, and a mutation that causes insertion of DNA into the fur gene;

(f) having reduced mnth gene expression caused by one or more of: a mutation that causes partial or full inactivation of the mnth gene, a mutation that causes partial or full deletion of the mnth gene, and a mutation that causes insertion of DNA into the mnth gene;

(g) having reduced fatc gene expression caused by one or more of: a mutation that causes partial or full inactivation of the fatc gene, a mutation that causes partial or full deletion of the fatc gene, and a mutation that causes insertion of DNA into the fatc gene; and (h) being resistant to tellurite, as determined by an ability to form a colony on M17 agar plates containing 0.1 mM $K_2TeO_3$.

4. The method of claim 1, wherein the mutant LAB has a perturbed divalent metal ion metabolism (DMIM) as compared to its mother strain.

5. The method of claim 4, wherein the divalent metal ion is selected from one or more of $Fe^{2+}$, $Mg^{2+}$, and $Mn^{2+}$.

6. The method of claim 1, wherein the mutant LAB has been obtained by mutagenesis.

7. The method of claim 1, wherein the mutant LAB has been obtained by genetic engineering.

8. The method of claim 1, wherein the mutant LAB has been obtained by a process comprising growth in a medium having a concentration of one or both of $Fe^{2+}$ and $Mn^{2+}$ of from 0 to below 0.25 µg/g.

9. The method of claim 1, wherein the mutant LAB belong to the species *Lactobacillus bulgaricus*.

10. The method of claim 1, wherein the mutant LAB belong to the species *Streptococcus thermophilus*.

11. The method claim 1, wherein the mutant LAB is selected from *Streptococcus thermophilus* strain CHCC15712 deposited at Deutsche Sammlung von Mikroorganismen and Zellkulturen GmbH, Braunschweig, Germany, under accession number DSM25955, and mutants thereof wherein less than 0.1% of the nucleotides in the bacterial genome of the mutant have been changed relative to CHCC15712 and wherein the mutant exhibits the same or improved properties with respect to exopolysaccharide (EPS) production as CHCC15712.

12. The method of claim 1, wherein the mutant LAB is provided in a composition comprising a metal ion chelator.

13. The method of claim 1, wherein the milk substrate has a concentration of one or both of $Fe^{2+}$ and $Mn^{2+}$ of from 0 to below 0.25 µg/g.

14. The method of claim 1, wherein the milk substrate comprises $Fe^{2+}$ ions and the method further comprises removing $Fe^{2+}$ ions from the milk substrate before, during or after inoculation with the mutant LAB, to obtain a milk substrate having a $Fe^{2+}$ concentration from 0 to below 0.25 µg/g.

15. The method of claim 1, wherein the milk substrate comprises $Mn^{2+}$ ions and the method further comprises removing $Mn^{2+}$ ions from the milk substrate before, during or after inoculation with the mutant LAB, to obtain a milk substrate having a $Mn^{2+}$ concentration from 0 to below 0.25 µg/g.

\* \* \* \* \*

UNITED STATES PATENT AND TRADEMARK OFFICE
CERTIFICATE OF CORRECTION

| | | |
|---|---|---|
| PATENT NO. | : 11,272,716 B2 | Page 1 of 1 |
| APPLICATION NO. | : 16/329727 | |
| DATED | : March 15, 2022 | |
| INVENTOR(S) | : Derkx et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 240 days.

Signed and Sealed this
Twentieth Day of December, 2022

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 19
<212> TYPE: DNA
<213> ORGANISM: Bacillus sp.
<220> FEATURE:
<223> OTHER INFORMATION: Fig 1a FURBOX Bacillus

<400> SEQUENCE: 1
gataatgata atcattatc                                              19

<210> SEQ ID NO 2
```

```
<211> LENGTH: 19
<212> TYPE: DNA
<213> ORGANISM: Streptococcus gordonii
<220> FEATURE:
<223> OTHER INFORMATION: Fig 1a FURBOX S. gordonii

<400> SEQUENCE: 2
gctatagaaa atgatagtt                                             19

<210> SEQ ID NO 3
<211> LENGTH: 19
<212> TYPE: DNA
<213> ORGANISM: Streptococcus thermophilus
<220> FEATURE:
<223> OTHER INFORMATION: Fig 1a FURBOX CHCC9844

<400> SEQUENCE: 3
tttgaaaaaa atgacaatt                                             19

<210> SEQ ID NO 4
<211> LENGTH: 600
<212> TYPE: DNA
<213> ORGANISM: Streptococcus thermophilus
<220> FEATURE:
<223> OTHER INFORMATION: Fig. 1 b

<400> SEQUENCE: 4
aaaaatattt ggaagaagaa gacttttaat aaataggtaa atatctgaca atttaaagtt     60
taactactaa aaatgtgaaa gatagttcac aatataatgg aaaatgatat aaattaaatg    120
attgatatca taatgaaaac gttttttttgt tttttttttga aaaaaatgac aattgaaatg    180
aaattgtatt aatgttacaa taataatggg gaatacttaa ttttaatttt taggagcaat    240
ttatatgagt tcgcgtacga atcgtaagca aaaacgtacg ggtaatagat catgggggat    300
ggtcaacgtt ggattgacca ttctgtatgc tattttagca ttggtcttat tattcaccat    360
gttcaattat aatttcctat cctttaggtt tttgaacatc attatcacta ttggtttgtt    420
ggtagttctt gctattagca tcttccttca gaagactaag aaatcaccac tagtgacaac    480
ggttgtattg gttatcttct cgctagtttc tctggttggt atttttggtt ttaaacaaat    540
gattgacatc actaaccgta tgaatcagac ggcagcattt tctgaagtag aaatgagcat    600
```